United States Patent [19]

Diehr et al.

[11] 4,455,428

[45] Jun. 19, 1984

[54] PREPARATION OF HETARYLOXYACETAMIDES

[75] Inventors: Hans-Joachim Diehr, Wuppertal; Uwe Priesnitz, Solingen, both of Fed. Rep. of Germany

[73] Assignee: Bayer Aktiengesellschaft, Leverkusen, Fed. Rep. of Germany

[21] Appl. No.: 442,924

[22] Filed: Nov. 18, 1982

[30] Foreign Application Priority Data

Dec. 10, 1981 [DE] Fed. Rep. of Germany ....... 3148839

[51] Int. Cl.$^3$ .......................................... C07D 277/34
[52] U.S. Cl. ..................... 548/187; 548/129; 548/132; 548/136; 548/144; 548/229; 548/251; 546/209; 546/174; 544/133; 544/137
[58] Field of Search ............... 548/187, 129, 132, 136, 548/144, 229, 251; 546/209, 174; 544/133, 137

[56] References Cited

FOREIGN PATENT DOCUMENTS 0018497 11/1980 European Pat. Off. .
0037938 10/1981 European Pat. Off. .
3038636 5/1982 Fed. Rep. of Germany .

OTHER PUBLICATIONS

Tetrahedron Letters, vol. 35, pp. 2169–2173, R. A. W. Johnstone et al.

Primary Examiner—Paul M. Coughlan, Jr.
Assistant Examiner—D. B. Springer
Attorney, Agent, or Firm—Sprung, Horn, Kramer & Woods

[57] ABSTRACT

A process for the preparation of a hetaryloxyacetamide of the formula

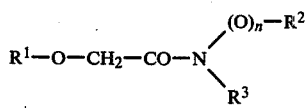

in which
$R^1$ is an optionally substituted oxazole, thiazole or tetrazole radical,
comprising reacting a hydroxyacetamide of the formula

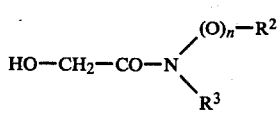

with a halogeno-hetarene of the formula

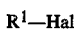

in which
Hal represents a fluorine, chlorine, bromine or iodine atom,
in the presence of solid, anhydrous potassium hydroxide and in the presence of an aprotic diluent at a temperature between about $-50°$ and $+50°$ C.

11 Claims, No Drawings

PREPARATION OF HETARYLOXYACETAMIDES

The invention relates to an unobvious process for the production of certain largely known herbicidal hetaryloxyacetamides.

It has already been disclosed that certain hetaryloxyacetamides are obtained when hydroxyacetamides are reacted with halogeno-hetarenes in the presence of potassium hydroxide in isopropanol, of potassium carbonate in acetonitrile, of potassium tert.-butanolate in tert.-butanol or of calcium oxide in dimethylsulphoxide (see DE-OS (German Published Specification) 2,914,003).

However, the yield and quality of the products prepared in this manner are in many cases unsatisfactory.

The present invention now provides a process for the production of a hetaryloxyacetamide of the general formula

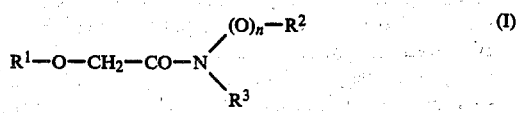

in which
- $R^1$ represents a five-membered heterocyclic radical which contains an oxygen or sulphur atom and in addition 1 to 3 nitrogen atoms and which is optionally substituted by halogen, cyano, nitro, amino, alkylamino, arylamino, dialkylamino, alkylcarbonylamino, alkylcarbonyl, carboxyl, alkoxycarbonyl, carbamoyl, alkylaminocarbonyl, dialkylaminocarbonyl, arylaminocarbonyl (which is optionally substituted by halogen, nitro or alkyl), aryl (which is optionally substituted by halogen, cyano, nitro, alkyl or alkoxy), aralkyl (which is optionally substituted by halogen), optionally halogen-substituted alkoxy, alkenoxy, alkinoxy, alkoxycarbonylalkoxy, aralkoxy or aryloxy, optionally halogen-substituted alkylthio, alkenylthio, alkinylthio, alkoxycarbonylalkylthio, aralkylthio or arylthio, optionally halogen-substituted alkylsulphinyl or alkylsulphonyl, optionally halogen-substituted alkyl, alkenyl, alkinyl, alkoxyalkyl, aralkoxyalkyl, aryloxyalkyl, alkylthioalkyl, alkylsulphinylalkyl, alkylsulphonylalkyl, arylthioalkyl, arylsulphinylalkyl, arylsulphonylalkyl, carboxyalkyl or alkoxycarbonylalkyl, or optionally substituted aminocarbonylalkyl, cyanoalkyl or cycloalkyl; or which is optionally benzo-fused, the benzo radical optionally being substituted by halogen, alkyl, halogenoalkyl, alkoxy, halogenoalkoxy, alkylthio, halogenoalkylthio, amino, alkylamino, dialkylamino, nitro, cyano, alkoxycarbonyl or optionally halogen-substituted alkylenedioxy, or in which
- $R^1$ represents a tetrazolyl radical which is substituted by phenyl (the phenyl radical optionally being substituted by halogen, cyano, nitro and/or by an optionally halogen-substituted radical selected from alkyl, alkoxy, alkylthio and alkylenedioxy), and in which
- n is 0 or 1 and
- $R^2$ and $R^3$, which can be identical or different, individually represent an optionally substituted radical selected from alkyl, alkenyl, alkinyl, cycloalk(en)yl, aralkyl and aryl, or, in the case where n is 0, $R^2$ and $R^3$ together with the nitrogen atom to which they are bonded, form an optionally substituted, optionally partially unsaturated and optionally benzo-fused monocyclic or bicyclic radical, which optionally contains further heteroatoms, which is characterized in that a hydroxyacetamide of the general formula

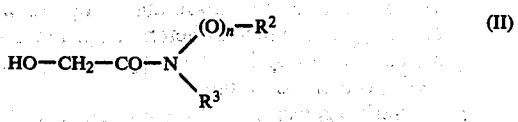

in which
- n, $R^2$ and $R^3$ have the abovementioned meanings, is reacted with a halogeno-hetarene of the general formula

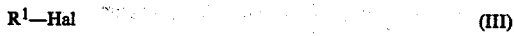

in which
- $R^1$ has the abovementioned meaning and
- Hal represents a fluorine, chlorine, bromine or iodine atom, in the presence of solid, anhydrous potassium hydroxide and in the presence of an aprotic diluent at a temperature between $-50°$ and $+50°$ C.

It is surprising that the hetaryloxyacetamides of the formula (I) are obtained in almost quantitative yields and in a high purity when solid potassium hydroxide, which is virtually insoluble in the aprotic medium, is used.

If, for example, hydroxyacetic acid dimethylamide and 2-bromobenzothiazole are used as starting substances, the course of the reaction in the process according to the invention can be outlined by the following equation:

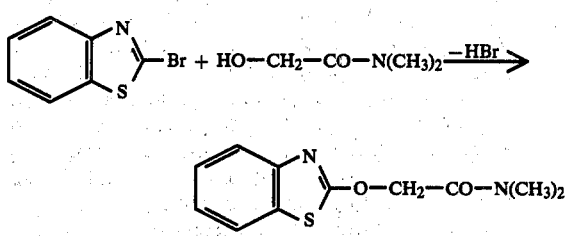

Preferred hydroxyacetamides of formula (II) to be used as starting substances are those
in which
- n is 0 or 1,
- $R^2$ represents an alkyl, alkoxyalkyl, alkenyl or alkinyl radical, in each case with up to 10 carbon atoms, or, in the case where n is 0, represents a cyanoalkyl or alkylthioalkyl radical, in each case with up to 10 carbon atoms, a cycloalkyl radical with 3 to 12 carbon atoms, an optionally halogen-substituted benzyl or phenethyl radical, or a phenyl radical which is optionally substituted by optionally halogen-substituted radical(s) selected from $C_1$ to $C_4$ alkyl, $C_1$ to $C_4$ alkoxy and $C_1$ to $C_4$ alkylthio,
- $R^3$ represents an alkyl, alkenyl, alkinyl, alkoxyalkyl, alkylthioalkyl or cyanoalkyl radical, in each case with up to 10 carbon atoms, a cycloalkyl radical with 3 to 12 carbon atoms, an optionally halogen-substituted benzyl radical, a phenethyl or naphthyl radical, or a phenyl radical which is optionally substituted by halogen, cyano, nitro or optionally halogen-substituted radical(s) selected from $C_1$ to $C_4$ alkyl, $C_1$ to $C_4$ alkoxy and $C_1$ to $C_4$ alkylthio, or the radicals $R^2$ and $R^3$, in the case where n is 0, together with the nitrogen atom to which they are bonded, form a saturated or partially unsaturated and/or benzo-fused monocyclic or bicyclic radical which has up to 15 carbon atoms, optionally contains oxygen as a further hetero-atom and is optionally substituted by 1 to 3 alkyl groups with in each case 1 to 5 carbon atoms.

Particularly preferred starting substances of formula (II) are those PS in which n is 0 or 1, $R^2$ represents a $C_1$ to $C_6$ alkyl, $C_1$ to $C_4$ alkoxyethyl, allyl, propargyl, 1-methylpropargyl or 1,1-dimethylpropargyl radical, or, in the case where n is 0, represents a cyanoethyl, cyclopentyl, cyclohexyl, benzyl or phenyl radical, and in which, furthermore, $R^3$ represents a $C_1$ to $C_6$ alkyl, $C_1$ to $C_4$ alkoxyethyl, allyl, propargyl, 1-methylpropargyl, 1,1-dimethylpropargyl, cyanoethyl, cyclopentyl, cyclohexyl, benzyl or naphthyl radical or a phenyl radical which has polysubstitution and mixed substitution by radical(s) selected from methyl, chlorine, cyano, nitro and methoxy, and in which, furthermore, the radicals $R^2$ and $R^3$, in the case where n is 0, together with the nitrogen atom to which they are bonded, represent a heterocyclic radical selected from pyrrolidyl, monoalkyl- or dialkyl-pyrrolidyl with 1 to 3 carbon atoms per alkyl group, morpholinyl or dialkylmorpholinyl with 1 to 3 carbon atoms per alkyl group, piperidyl, monoalkyl-, dialkyl- or trialkyl-piperidyl with 1 to 3 carbon atoms per alkyl group, perhydroazepinyl (hexamethyleneimino radical), trimethyl-perhydroazepinyl, the heptamethyleneimino radical, the dodecamethyleneimino radical, indolinyl, monoalkyl-, dialkyl- or trialkyl-indolinyl with up to 3 carbon atoms per alkyl group, perhydroindolyl, monoalkyl-, dialkyl- or trialkyl-perhydroindolyl with 1 to 3 carbon atoms per alkyl group, 1,2,3,4-tetrahydroquinolyl or 1,2,3,4-tetrahydro-isoquinolyl, monoalkyl-, dialkyl- or trialkyl-1,2,3,4-tetrahydro-quinolyl or -isoquinolyl with 1 to 3 carbon atoms per alkyl group, perhydroquinolyl or perhydroisoquinolyl, and monoalkyl-, dialkyl- or trialkyl-perhydroquinolyl or -perhydroisoquinolyl with 1 to 3 carbon atoms per alkyl group.

Examples which may be mentioned of starting compounds of the formula (II) are: N-methoxy-N-methyl-, N-ethoxy-N-methyl-, N-n-propoxy-N-methyl-, N-iso-propoxy-N-methyl-, N-ethoxy-N-ethyl-, N-n-propoxy-N-ethyl-, N-isopropoxy-N-ethyl-, N-n-propoxy-N-n-propyl-, N-iso-propoxy-N-isopropyl-, N-iso-propoxy-N-n-propyl, N-methoxy-N-ethyl-, N-methoxy-N-n-propyl-, N-methoxy-N-isopropyl-, N-methoxy-N-n-butyl-, N-methoxy-N-isobutyl-, N-methoxy-N-sec-butyl-, N-methoxy-N-sec-hexyl-, N-ethoxy-N-n-propyl-, N-ethoxy-N-isopropyl-, N-(2-ethoxy-ethoxy)-N-methyl-, N-(2-ethoxy-ethoxy)-N-ethyl-, N-(2-ethoxy-ethoxy)-N-n-propyl-, N-(2-ethoxy-ethoxy)-N-isopropyl-, N-(2-ethoxy-ethoxy)-N-cyclohexyl-, N-allyloxy-N-allyl-, N-allyloxy-N-methyl-, N-allyloxy-N-ethyl-, N-allyloxy-N-n-propyl-, N-allyloxy-N-isopropyl-, N-allyloxy-N-n-butyl-, N-allyloxy-N-iso-butyl-, N-allyloxy-N-sec-butyl-, N-methoxy-N-cyclopentyl-, N-methoxy-N-cyclohexyl-, N-methoxy-N-(2-ethoxy-ethyl)-, N-ethoxy-N-(2-ethoxy-ethyl)-, N-(2-ethoxy-ethoxy)-N-(2-ethoxy-ethyl)- and N-(2-ethoxy-ethoxy)-N-sec-hexylhydroxyacetic acid amide, and hydroxyacetic acid dimethylamide, diethylamide, di-n-propylamide, di-isopropylamide, N-methyl-N-iso-propylamide, N-methyl-N-iso-butylamide, N-methyl-N-sec-butylamide, di-(2-ethyl-hexyl)-amide, N-methyl-N-(2-cyano-ethyl)-amide, di-(2-methoxy-ethyl)-amide, di-allylamide, N-methyl-N-propargylamide, N-methyl-N-(1-methyl-propargyl)-amide, dipropargylamide, N-methyl-N-cyclopentylamide, N-methyl-N-cyclohexylamide, N-methyl-anilide, N-methyl-N-(2-methyl-phenyl)-, N-methyl-N-(3-methyl-phenyl)- and N-methyl-N-(4-methyl-phenyl)-amide, N-methyl-N-(2-chlorophenyl)-, N-methyl-N-(3-chlorophenyl)- and N-methyl-N-(4-chloro-phenyl)-amide, N-methyl-N-(3-nitro-6-methylphenyl)-amide, N-ethyl-anilide, N-ethyl-N-(2-methylphenyl)-, N-ethyl-N-(3-methylphenyl)- and N-ethyl-N-(B 4-methyl-phenyl)-amide, N-ethyl-N-(2-chlorophenyl)-, N-ethyl-N-(3-chloro-phenyl)- and N-ethyl-N-(4-chloro-phenyl)-amide, N-ethyl-N-(3-nitro-6-methylphenyl)-amide, N-propyl-anilide, N-propyl-N-(2-methyl-phenyl)-, N-propyl-N-(3-methyl-phenyl)- and N-propyl-N-(4-methyl-phenyl)-amide, N-propyl-N-(2-chlorophenyl)-, N-propyl-N-(3-chloro-phenyl)- and N-propyl-N-(4-chloro-phenyl)-amide, N-iso-propyl-N-(2-methylphenyl)-, N-iso-propyl-N-(3-methyl-phenyl)- and N-iso-propyl-N-(4-methyl-phenyl)-amide, N-iso-propyl-N-(3-nitro-6-methyl-phenyl)-amide, N-butyl-anilide, N-butyl-N-(2-methyl-phenyl)-, N-butyl-N-(3-methylphenyl)- and N-butyl-N-(4-methyl-phenyl)-amide, N-butyl-N-(2-chloro-phenyl)-, N-butyl-N-(3-chloro-phenyl) and N-butyl-N-(4-chloro-phenyl)-amide, N-isobutyl-N-(2-methyl-phenyl)-, N-iso-butyl-N-(3-methylphenyl)- and N-iso-butyl-N-(4-methyl-phenyl)-amide, N-iso-butyl-N-(3-nitro-6-methyl-phenyl)-amide, N-methyl-N-naphth-1-yl-amide, N-methyl-N-naphth-2-yl-amide, N-ethyl-N-naphth-1-yl-amide, N-ethyl-N-naphth-2-yl-amide, N-n-propyl-N-naphth-2-yl-amide, N-iso-propyl-N-naphth-2-yl-amide, N-n-butyl-N-naphth-2-yl-amide, N-isobutyl-N-naphth-2-yl-amide, dibenzylamide, N-methyl-N-benzylamide, N-ethyl-N-benzylamide, N-propyl-N-benzylamide, N-butyl-N-benzylamide, pyrrolidide, 2-methyl-pyrrolidide, morpholide, 3,5-dimethyl-morpholide, piperidide, 2-methyl-piperidide, 4-methyl-piperidide, 2,4-dimethyl-piperidide, 2,4-dimethyl-piperidide, 2,4,6-trimethyl-piperidide, 2-ethyl-piperidide, 4-ethyl-piperidide, 2,4-diethyl-piperidide, 2,4,6-triethyl-piperidide, 2-methyl-4-ethyl-piperidide, 2-ethyl-4-methyl-piperidide, 2-methyl-5-ethyl-piperidide, 2-ethyl-5-methyl-piperidide, 2-methyl-6-ethyl-piperidide, indolinide, 2-methyl-1,2,3,4-tetrahydroquinolide, perhydroindolide, 2-methyl-perhydroindolide, 2,2-dimethyl-perhydroindolide, 1,2,3,4-tetrahydroquinolide, 1,2,3,4-tetrahydro-isoquinolide and perhydroisoquinolide.

Hydroxyacetamides of the formula (II) are known and can be prepared by processes which are in themselves known (see European Pat. Nos. 5,501 and 18,497 and DE-OS (German Published Specifications) Nos. 2,904,490 and 2,946,524).

Preferred halogeno-hetarenes of formula (II) also to be used as starting compounds are those, in which Hal represents a chlorine or bromine atom and $R^1$ represents a radical of the general formula $$\begin{array}{c} D-A \\ \vdots \quad C- \\ E-G \end{array}$$

wherein

C represents carbon,

A represents $C-R^4$ or N,

D represents $C-R^5$ or N,

E represents $C-R^6$, N, O or S and

G represents $C-R^7$, N, O or S, with the proviso that at least one of the ring members (A, D, E or G) represents N and at least one of the ring members represents O or S, and wherein the radicals $R^4$, $R^5$, $R^6$ and $R^7$, which can be identical or different, individually represent a hydrogen or halogen atom or a nitro, cyano, amino, $C_1$ to $C_4$ alkyl-amino, di-($C_1$ to $C_4$ alkyl)-amino, $C_1$ to $C_4$ alkyl-carbonylamino, $C_1$ to $C_4$ alkyl-carbonyl, carboxyl, $C_1$ to $C_4$ alkoxy-carbonyl, carbamoyl, $C_1$ to $C_4$ alkylamino-carbonyl, di-($C_1$ to $C_4$ alkyl)-amino-carbonyl, phenyl-amino-carbonyl (which is optionally substituted by halogen, nitro or $C_1$ to $C_4$ alkyl), phenyl (which is optionally substituted by halogen, nitro, cyano, $C_1$ to $C_4$ alkyl or $C_1$ to $C_4$ alkoxy), optionally halogen-substituted benzyl or phenethyl, optionally halogen-substituted $C_1$ to $C_4$ alkoxy, $C_2$ to $C_4$ alkenoxy, $C_2$ to $C_4$ alkinoxy, $C_1$ to $C_4$ alkoxycarbonylmethoxy, benzyloxy or phenoxy, optionally halogen-substituted $C_1$ to $C_4$ alkylthio, $C_2$ to $C_4$ alkenylthio, $C_2$ to $C_4$ alkinylthio, $C_1$ to $C_4$ alkoxy-carbonyl-methylthio, benzylthio, phenylthio, $C_1$ to $C_4$ alkylsulphinyl or $C_1$ to $C_4$ alkylsulphonyl, optionally halogen-substituted $C_1$ to $C_6$ alkyl, $C_3$ to $C_6$ alkenyl or $C_3$ to $C_6$ alkinyl, cyano $C_1$ to $C_4$ alkyl, $C_1$ to $C_4$ alkoxy-$C_1$ or $C_2$ alkyl, phenoxy- or phenylthio-methyl, benzyloxy- or benzylthio-methyl, $C_1$ to $C_4$ alkylthio-$C_1$ or $C_2$ alkyl, $C_1$ to $C_4$ alkyl- or phenyl-sulphinyl-$C_1$ or $C_2$ alkyl, $C_1$ to $C_4$ alkyl- or phenyl-sulphonyl-$C_1$ or $C_2$ alkyl, carboxy-$C_1$ or $C_2$ alkyl, $C_1$ to $C_4$ alkoxycarbonyl-$C_1$ or $C_2$ alkyl, $C_1$ to $C_4$ alkyl-aminocarbonyl-$C_1$ or $C_2$ alkyl, di($C_1$ to $C_4$ alkyl)-amino-carbonyl-$C_1$ or $C_2$ alkyl, phenylaminocarbonyl-$C_1$ or $C_2$ alkyl or $C_3$ to $C_{12}$ cycloalkyl, or wherein in each case two adjacent radicals $R^4$ and $R^5$, or $R^5$ and $R^6$, or $R^6$ and $R^7$, together represent a fused-on benzo radical, which can be substituted by halogen, nitro, cyano or optionally halogen-substituted radical(s) selected from $C_1$ to $C_4$ alkyl, $C_1$ to $C_4$ alkoxy, $C_1$ to $C_4$ alkylthio and $C_1$ or $C_2$ alkylenedioxy;

$R^1$ furthermore preferably represents a radical of the general formula $$\begin{array}{c} N-N \\ \parallel \quad \diagdown \\ N-N \\ | \\ \bigcirc \\ R_p'' \end{array}$$

wherein p is 1, 2, 3, 4 or 5 and

R" represents a hydrogen or halogen atom, a cyano or nitro radical and/or an optionally, halogen-substituted radical selected from $C_1$ to $C_4$ alkyl, $C_1$ to $C_4$ alkoxy, $C_1$ to $C_4$ alkylthio and $C_1$ or $C_2$ alkylenedioxy.

Particularly preferred starting substances of formula (III) are those in which

Hal represents a chlorine atom and $R^1$ represents one of the following azolyl radicals $$\begin{array}{ccc} R^8 \!-\!\!\!=\!\!\!\underset{R^9}{\overset{N}{\diagup}}\!\!\!-\!\!X\!\!-\!\! , & R^{10}\!-\!\!\!\underset{N}{\overset{N}{\diagup}}\!\!\!-\!\!X\!\!-\!\! , & \underset{R^{11}}{\overset{N-N}{\diagup}}\!\!-\!\!X\!\!-\!\! , \end{array}$$

$$\begin{array}{cc} R^{13}\!\!\underset{R^{14}}{\overset{R^{12}}{\diagup}}\!\!\underset{R^{15}}{\overset{N}{\diagup}}\!\!\!-\!\!X\!\!-\!\! & \text{or} & R^{20}\!\!\underset{R^{19}}{\overset{N-N}{\diagup}}\!\!\underset{R^{18}}{\overset{N-N}{\diagdown}}\!\!-\!\!\underset{R^{17}}{\overset{R^{16}}{\diagup}} \end{array}$$

wherein

X in each case represents an oxygen or sulphur atom the radicals $R^8$, $R^9$, $R^{10}$ and $R^{11}$, which can be identical or different, individually represent a hydrogen atom or a nitro, cyano, $C_1$ to $C_3$ alkylcarbonyl, $C_1$ to $C_3$ alkoxy-carbonyl, phenyl (which is optionally monosubstituted or disubstituted by fluorine, chlorine, bromine, methyl, methoxy, nitro, amino and/or cyano), phenoxy, phenylthio, $C_1$ to $C_3$ alkylthio, $C_1$ to $C_3$ alkoxy, $C_1$ to $C_3$ alkylsulphinyl, $C_1$ to $C_3$ alkyl-sulphonyl, $C_1$ to $C_4$ alkyl, trifluoromethyl, cyano-$C_1$ to $C_4$ alkyl, $C_2$ to $C_4$ alkenyl, benzyloxymethyl, $C_1$ to $C_3$ alkyl-amino, N-$C_1$ to $C_3$ alkyl-N-$C_1$ to $C_4$ alkyl-carbonylamino, phenoxymethylbenzylthio or $C_1$ to $C_3$ alkyl-carbonyloxy radical and the radicals $R^{12}$ to $R^{20}$, which can be identical or different, individually represent a hydrogen, bromine or chlorine atom or a nitro, $C_1$ to $C_2$ alkyl, $C_1$ or $C_2$ alkoxy, trifluoromethyl or trifluoromethoxy radical.

Examples which may be mentioned of starting substances of the formula (III) are: 2-chloro- and 2-bromooxazole and -thiazole, 2,4-dichloro-, 2,5-dichloro- and 2,4,5-trichloro-oxazole and -thiazole, 4-methyl-, 5-methyl-, 4-tert-butyl-, 4,5-dimethyl-, 4-methyl-5-cyano-, 4-methyl-5-chloro-, 5-methyl-4-chloro-, 4-methyl-5-methoxycarbonyl-, 4-methyl-5-ethoxycarbonyl-, 4-methyl-5-isopropoxycarbonyl-, 4-methyl-5-acetyl-, 5-phenyl-, 4,5-diphenyl-, 4-chloro-5-phenyl-, 4-chloro-5-(3,4-dichlorophenyl)- and 4-methyl-5-phenylthio-2-chlorooxazole, -2-bromo-oxazole, -2-chloro-thiazole and -2-bromo-thiazole; 3-tert-butyl-4-cyano-, 3-but-3-en-1-yl-, 3,4-bis-ethoxycarbonyl-, 3-phenyl- and 3-ethyl-4-phenyl-5-chloro-isoxazole, -5-chloro-isothiazole, -5-bromo-isoxazole and -5-bromoisothiazole; 3,5-bis-ethoxycarbonyl-4-chloro- and 3,5-bis-ethoxycarbonyl-4-bromo-isoxazole and -iso-thiazole; 3,5-dichloro-1,2,4-oxadiazole, 3-methyl-, 3-ethyl-, 3-n-propyl-, 3-iso-propyl-, 3-tert-butyl-, 3-trifluoromethyl-, 3-trichloromethyl-, 3-methylthio-, 3-methylsulphinyl-, 3-methylsulphonyl- and 3-benzylthio-5-chloro-1,2,4-thiadiazole and -5-bromo-1,2,4-thiadiazole; 4-methyl-, 4-ethyl-, 4-n-propyl- and 4-isopropyl-3-chloro-1,2,5-thiadiazole and -3-bromo-1,2,5-thiadiazole; 2-chloro- and 2-bromo-1,3,4-oxadiazole, 2-chloro- and 2-bromo-5-phenyl-1,3,4-thiadiazole, 5-methyl-, 5-ethyl-, 5-n-propyl-, 5-propylthio-, 5-iso-propyl-, 5-tert-butyl-, 5-bromo-, 5-methylsulphinyl-, 5-ethylsulphinyl-, 5-propylsulphinyl-, 5-methyl-sulphonyl-, 5-ethyl-sulphonyl-, 5-propyl-sulphonyl-, 5-methoxycarbonyl-, 5-ethoxy-carbonyl-, 5-(1-cyano-2-methyl-propyl)-, 5-benzyloxymethyl-, 5-acetylamino-, 5-nitro-, 5-propylthio-, 5-trifluoromethyl-, 5-trichloromethyl-, 5-methylamino- and 5-(N-methyl-N-tert-butylcarbonyl-amino)-2-chloro-1,3,4-oxadiazole, -2-bromo-1,3,4-oxadiazole, -2-chloro-1,3,4-thiadiazole and -2-bromo-1,3,4-thiadiazole; 2-chloro- and 2-bromo-benzoxazole, 2-chloro- and 2-bromo-benzothiazole; 5-methyl-2-chloro-benzoxazole, 2-chloro-6-ethoxy-benzothiazole, 2,5-dichloro-benzoxazole, 2-chloro-6-trifluoromethyl-benzothiazole, 2-chloro-5-trifluoromethoxy-benzothiazole, 2-chloro-5,6-difluoromethylenedioxy-benzothiazole, 2,4,6,7-tetrachlorobenzothiazole, 2-chloro-4,6-difluorobenzothiazole, 2-chloro-5-nitro-benzothiazole, 2-chloro-6-nitro-benzothiazole, 2-chloro-5-nitro-benzoxazole, 2-chloro-5-cyano-benzoxazole and 5-chloro-1-phenyl(1H-)tetrazole.

Halogenoazoles of the formula (III) are known (see Elderfield, Heterocyclic Compounds Volume 5 (1957), page 298 and page 452; Volume 7 (1961), page 463 and page 541; Weissberger, The Chemistry of Heterocyclic Compounds, (a) 'Five-Membered Heterocyclic Compounds with Nitrogen and Sulphur or Nitrogen, Sulphur and Oxygen' (1952), page 35 and page 81, (b) 'Five and Six-Membered Compounds with Nitrogen and Oxygen' (1962), page 5, page 245 and page 263; Advances in Heterocyclic Chemistry, Volume 5 (1965), page 119; Volume 7 (1966), page 183; Volume 17 (1974), page 99 and Volume 20 (1976), page 65; Synthesis 1978, 803; Tetrahedron Letters 1968, 829; Chem. Ber. 89 (1956), 1534; 90 (1957), 182; 92 (1959), 1928; J. Org. Chem. 27 (1962), 2589; DE-OS'en (German Published Specifications) 1,670,706, 1,164,413 and 2,213,865; DE-AS (German Published Specification) 1,251,327; and British Patent Specification 1,128,025).

It is very especially preferred that the process according to the invention is carried out using hydroxyacetic acid N,N-diethylamide as the hydroxyacetamide of formula (II) and 2,4,5-trichlorothiazole as the halogeno-hetarene of formula (III).

The process according to the invention is carried out using an aprotic diluent. Possible diluents are, above all, the following groups of organic solvents: aromatic, optionally halogenated hydrocarbons (such as benzene, toluene, xylene, chlorobenzene and o-dichlorobenzene), ethers (such as diethyl ether, dipropyl ether, di-isopropyl ether, dibutyl ether, di-isobutyl ether, methyl propyl ether, methyl isopropyl ether, methyl butyl ether, methyl isobutyl ether, tetrahydrofuran and dioxane), dialkyl ketones (such as acetone, methyl ethyl ketone, methyl propyl ketone, methyl isopropyl ketone, methyl butyl ketone and methyl isobutyl ketone), carboxylic acid esters and amides (such as ethyl acetate, propyl acetate, butyl acetate, dimethylformamide and dimethylacetamide), and sulphoxides and sulphones (such as dimethylsulphoxide and tetramethylene sulphone (sulpholane)).

The potassium hydroxide used as the acid-binding agent in the process according to the invention is employed in anhydrous, solid form. Potassium hydroxide flakes or potassium hydroxide lozenges are preferably used.

The reaction temperature can be varied within the substantial range between −50° and +50° C., and is preferably between −20° and +10° C.

For carrying out the process according to the invention, in general between 1 and 2 mols, preferably between 1.0 and 1.5 mols, of hydroxyacetamide of the formula (II) and between 1 and 3 mols, preferably between 1.2 and 2.0 mols, of potassium hydroxide are employed per mol of halogeno-hetarene of the formula (III).

In a preferred embodiment of the process according to the invention, the potassium hydroxide is initially introduced into the diluent and the starting substances of the formulae (II) and (III) are added simultaneously, or successively with the substance of formula (II) being added before the substance of formula (III). The reaction mixture is stirred until the reaction has ended.

Working up can be carried out by customary methods, for example by dilution with an organic solvent which is virtually immiscible with water (such as toluene), washing with dilute hydrochloric acid and then with water, separating off the organic phase and distilling off the solvent. The crude products which remain can be further purified by customary methods if required.

The active compounds of the formula (I) to be prepared by the process according to the invention can be used as herbicides (see European Pat. Nos. 5,501 and 18,497 and DE-OS (German Published Specifications) Nos. 2,822,155, 2,903,966, 2,914,003, 2,946,432, 2,946,524 and 3,004,326).

The active compounds according to the invention influence plant growth and can therefore be used as defoliants, desiccants, agents for destroying broad-leaved plants, germination inhibitors and, especially, as weedkillers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monocharia, Fimbristylis, Sagittaria, Eleocharis, Scirpus, Paspalum, Ischaemum, Spenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

For combating weeds, the active compounds according to the invention can be used, as such or in their formulations, in admixture with other herbicides, it being possible to use finished formulations or tank mixing.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used nonionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The present invention also provides a herbicidal composition containing as active ingredient a compound of the present invention in admixture with a solid diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The following examples illustrate the practice of the invention:

EXAMPLE 1

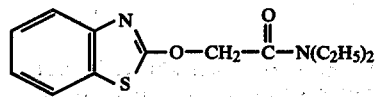 (I)

19.7 g (0.15 mol) of hydroxyacetic acid N,N-diethylamide were added dropwise to a mixture, which had been cooled to 0° to 5° C., of 11.2 g (0.2 mol) of potassium hydroxide lozenges (12.7 g of 88% pure product)

and 50 ml of toluene, and the mixture was stirred at 0° to 5° C. for 30 minutes. 17 g (0.1 mol) of 2chloro-benzothiazole (dissolved in 50 ml of toluene) were then added dropwise and the reaction mixture was stirred at 0° to 5° C. for a further 3 hours. Toluene was then added in an amount such that a clear solution was formed, the solution was washed with 200 ml of dilute hydrochloric acid and then with water (2×250 ml) and the solvent was distilled off under reduced pressure. 26.4 g (100% of theory) of 2-benzothiazolyl-oxyacetic acid N,N-diethylamide of melting point 62° to 63° C. were obtained.

EXAMPLE 2

(2) [Structure: 4,5-dichloro-2-thiazolyl-oxyacetic acid N,N-diethylamide]
Cl—C=C(Cl)—S—C(=N)—O—CH$_2$—CO—N(C$_2$H$_5$)$_2$ 37.8 g (0.2 mol) of 2,4,5-trichlorothiazole and 28.8 g (0.22 mol) of hydroxyacetic acid N,N-diethylamide were added dropwise to a mixture, cooled to −15° C., of 16.8 g (0.3 mol) of potassium hydroxide lozenges (19.1 g of 88% pure product) and 100 ml of methyl isobutyl ketone. The mixture was stirred at −15° C. for 30 minutes and then at −5° C. for 1 hour. 200 ml of methyl isobutyl ketone were added and the mixture was washed with 150 ml of dilute hydrochloric acid and then with water (2×250 ml). The solvent was distilled off under reduced pressure. 54.9 g (97% of theory) of 4,5-dichloro-2-thiazolyl-oxyacetic acid N,N-diethylamide of melting point 44° to 45° C. were obtained.

EXAMPLE 3

(3) [Structure: 3-tert.-butyl-5-(1,2,4-thiadiazolyl)-oxyacetic acid N-(1,2,3,4-tetrahydroquinolide)]
tert-C$_4$H$_9$—C=N—N=C(S)—O—CH$_2$—CO—N(tetrahydroquinoline)

89.4 g (0.5 mol) of 3-tert.-butyl-5-chloro-1,2,4-thiadiazole and 95.7 g (0.5 mole) of hydroxyacetic acid N-(1,2,3,4-tetrahydroquinolide), dissolved in 500 ml of tetrahydrofuran, were added dropwise to a mixture, cooled to −5° C., of 44.9 g (0.8 mol) of potassium hydroxide lozenges (51 g of 88% pure product) and 200 ml of tetrahydrofuran, while stirring vigorously. The reaction mixture was subsequently stirred at −5° C. for 2 hours and, after being warmed to 20° C., for another hour at 20° C. 300 ml of xylene were added and the mixture was washed with 250 ml of water. The aqueous phase was then extracted with xylene. The combined organic phases were washed with dilute hydrochloric acid and then with water. The solvent was removed under reduced pressure. 155 g (86% of theory) of 3-tert.-butyl-5-(1,2,4-thiadiazolyl)-oxyacetic acid N-(1,2,3,4-tetrahydroquinolide) of melting point 66° to 67° C. were obtained.

The compounds below could be obtained in an analogous manner:

(4) Cl—C=C(Cl)—S—C(=N)—O—CH$_2$—CO—N(CH$_3$)(C$_4$H$_9$-n)
Melting point 41 to 42° C.

(5) Cl—C=C(Cl)—S—C(=N)—O—CH$_2$—CO—N(CH$_2$—CH=CH$_2$)$_2$
Melting point 44 to 45° C.

(6) [benzothiazolyl]—O—CH$_2$—CO—N(CH$_2$—CH=CH$_2$)$_2$
Melting point 73 to 74° C.

It will be appreciated that the instant specification and examples are set forth by way of illustration and not limitation, and that various modifications and changes may be made without departing from the spirit and scope of the present invention.

We claim:

1. In the preparation of a hetaryloxyacetamide of the formula $$R^1-O-CH_2-CO-N\begin{pmatrix}(O)_n-R^2\\R^3\end{pmatrix}$$

in which
R$^1$ represents a five-membered heterocyclic radical which contains an oxygen or sulphur atom and in addition 1 to 3 nitrogen atoms and which is optionally substituted by halogen, cyano, nitro, amino, alkylamino, arylamino, dialkylamino, alkylcarbonylamino, alkylcarbonyl, carboxyl, alkoxycarbonyl, carbamoyl, alkylaminocarbonyl, dialkylaminocarbonyl, arylaminocarbonyl (which is optionally substituted by halogen, nitro or alkyl), aryl (which is optionally substituted by halogen, cyano, nitro, alkyl or alkoxy), aralkyl (which is optionally substituted by halogen), optionally halogen-substituted alkoxy, alkenoxy, alkinoxy, alkoxycarbonylalkoxy, aralkoxy or aryloxy, optionally halogen-substituted alkylthio, alkenylthio, alkinylthio, alkoxycarbonylalkylthio, aralkylthio or arylthio, optionally halogen-substituted alkylsulphinyl or alkylsulphonyl, optionally halogen-substituted alkyl, alkenyl, alkinyl, alkoxyalkyl, aralkoxyalkyl, aryloxyalkyl, alkylthioalkyl, alkylsulphinylalkyl, alkylsulphonylalkyl, arylthioalkyl, arylsulphinylalkyl, arylsulphonylalkyl, carboxyalkyl or alkoxycarbonylalkyl, or optionally substituted aminocarbonylalkyl, cyanoalkyl or cycloalkyl, or which is optionally benzo-fused, the benzo radical optionally being substituted by halogen, alkyl, halogenoalkyl, alkoxy, halogenoalkoxy, alkylthio, halogenoalkylthio, amino, alkylamino, dialkylamino, nitro, cyano, alkoxycarbonyl or optionally halogensubstituted alkylenedioxy, or in which $R^1$ represents a tetrazolyl radical which is substituted by phenyl (the phenyl radical optionally being substituted by halogen, cyano, nitro and/or by an optionally halogen-substituted radical selected from alkyl, alkoxy, alkylthio and alkylenedioxy), and in which n is 0 or 1 and $R^2$ and $R^3$, which can be identical or different, individually represent an optionally substituted radical selected from alkyl, alkenyl, alkinyl, cycloalk(en)yl, aralkyl and aryl, or, in the case where n is 0, $R^2$ and $R^3$ together with the nitrogen atom to which they are bonded, form an optionally substituted, optionally partially unsaturated and optionally benzo-fused monocyclic or bicyclic radical, which optionally contains further heteroatoms, by reacting a hydroxyacetamide of the formula

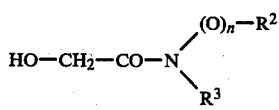

with a halogeno-hetarene of the formula $R^1$-Hal in which

Hal represents a fluorine, chlorine, bromine or iodine atom, in the presence of potassium hydroxide and in the presence of a diluent at a temperature between about $-50°$ and $+50°$ C., the improvement which comprises using the potassium hydroxide in the form of solid anhydrous potassium hydroxide and using an aprotic diluent in which the potassium hydroxide is virtually insoluble.

2. A process according to claim 1, wherein the reaction is carried out at a temperature between about $-20°$ and $+10°$ C.

3. A process according to claim 1, wherein about 1 to 2 mols of the hydroxyacetamide are employed per mol of the halogeno-hetarene.

4. A process according to claim 1, wherein about 1 to 1.5 mols of the hydroxyacetamide are employed per mol of the halogeno-hetarene.

5. A process according to claim 1, wherein about 1 to 3 mols of potassium hydroxide are employed per mol of halogeno-hetarene.

6. A process according to claim 1, wherein about 1.2 to 2 mols of potassium hydroxide are employed per mol of halogeno-hetarene.

7. A process according to claim 1, wherein an optionally chlorinated hydrocarbon, an ether, a dialkyl ketone, a carboxylic acid alkyl ester, a carboxylic acid amide, a sulphoxide or a sulphone is used as the aprotic diluent.

8. A process according to claim 1, wherein hydroxyacetic acid N,N-diethylamide is employed as the hydroxyacetamide and 2,4,5-trichlorothiazole is employed as the halogeno-hetarene.

9. A process according to claim 1, wherein the potassium hydroxide is initially introduced into the aprotic diluent, the hydroxyacetamide is then added, and the halogeno-hetarene is then added either simultaneously with or after the hydroxyacetamide, while stirring.

10. A process according to claim 9, wherein hydroxyacetic acid N,N-diethylamide is employed as the hydroxyacetamide and 2,4,5-trichlorothiazole is employed as the halogeno-hetarene, the reaction is carried out at a temperature between about $-20°$ and $+10°$ C., about 1 to 1.5 mols of the hydroxyacetamide are employed per mol of the halogeno-hetarene, about 1.2 to 2 mols of potassium hydroxide are employed per mol of halogeno-hetarene, and an optionally chlorinated hydrocarbon, an ether, a dialkyl ketone, a carboxylic acid alkyl ester, a carboxylic acid amide, a sulphoxide or a sulphone is used as the aprotic diluent.

11. A process according to claim 1, wherein the solid anhydrous potassium hydroxide is in the form of lozenges.

* * * * *